(12) United States Patent
Fujiwara et al.

(10) Patent No.: US 8,460,616 B2
(45) Date of Patent: Jun. 11, 2013

(54) ANALYZER, METHOD FOR CLEANING PHOTOMETRY MECHANISM IN SUCH ANALYZER, AND CLEANING TOOL

(75) Inventors: Toshinori Fujiwara, Kyoto (JP); Hideki Tanji, Kyoto (JP); Naoyuki Usagawa, Kyoto (JP)

(73) Assignee: Arkray, Inc., Kyoto-Shi (JP)

( * ) Notice: Subject to any disclaimer, the term of this patent is extended or adjusted under 35 U.S.C. 154(b) by 774 days.

(21) Appl. No.: 11/918,831

(22) PCT Filed: Apr. 19, 2006

(86) PCT No.: PCT/JP2006/308192
§ 371 (c)(1),
(2), (4) Date: Oct. 19, 2007

(87) PCT Pub. No.: WO2006/112470
PCT Pub. Date: Oct. 26, 2006

(65) Prior Publication Data
US 2009/0052033 A1 Feb. 26, 2009

(30) Foreign Application Priority Data
Apr. 20, 2005 (JP) .................. 2005-121833

(51) Int. Cl.
*G01N 15/06* (2006.01)
*G01N 33/00* (2006.01)
*G01N 33/48* (2006.01)

(52) U.S. Cl.
USPC ......... 422/400; 422/50; 422/68.1; 422/82.05; 422/82.09; 436/43; 436/164; 436/169; 436/172

(58) Field of Classification Search
USPC .............................. 422/50, 55, 82.05; 436/164
See application file for complete search history.

(56) References Cited

U.S. PATENT DOCUMENTS

| 4,702,826 | A | * | 10/1987 | Pogue ........................... 209/237 |
| 5,039,615 | A | | 8/1991 | Takahata |
| 5,185,531 | A | | 2/1993 | Wynn |
| 5,993,560 | A | * | 11/1999 | Wasak et al. ....................... 134/6 |
| 6,027,570 | A | * | 2/2000 | Farr et al. ........................... 134/2 |
| 6,071,739 | A | | 6/2000 | Vadgama et al. |

(Continued)

FOREIGN PATENT DOCUMENTS

| CH | 591 078 | 8/1977 |
| EP | 0 296 846 | 12/1988 |

(Continued)

OTHER PUBLICATIONS

International Search Report from the corresponding PCT/JP2006/308192, May 16, 2006.

*Primary Examiner* — Brian J Sines
(74) *Attorney, Agent, or Firm* — Fox Rothschild LLP

(57) ABSTRACT

The present invention relates to an analyzer (1) including a photometry mechanism (6) for photometrically analyzing a reagent pad of an analytical tool to which a sample is applied, and a table (4) including a placing portion (41) at which the analytical tool is to be placed. The light emitting surface (68) or the light incident surface (68) of the light from the light emitting elements (66) of the photometry mechanism (6) is cleaned, with a cleaning tool (22) placed at the table (4). The present invention further provides a cleaning tool (22) for cleaning the photometry mechanism (6) of the analyzer (1).

8 Claims, 18 Drawing Sheets

| U.S. PATENT DOCUMENTS | | | | FOREIGN PATENT DOCUMENTS | | |
|---|---|---|---|---|---|---|
| 6,201,607 B1 | 3/2001 | Roth et al. | | EP | 0 447 888 | 9/1991 |
| 6,239,445 B1 | 5/2001 | Shaeef | | JP | 2003-227752 | 8/2003 |
| 6,261,522 B1 * | 7/2001 | Hough et al. | 422/82.05 | WO | WO 88/07679 | 10/1988 |
| 6,394,952 B1 * | 5/2002 | Anderson et al. | 600/300 | | | |
| 6,736,926 B2 * | 5/2004 | Chopra et al. | 156/345.13 | | | |

\* cited by examiner

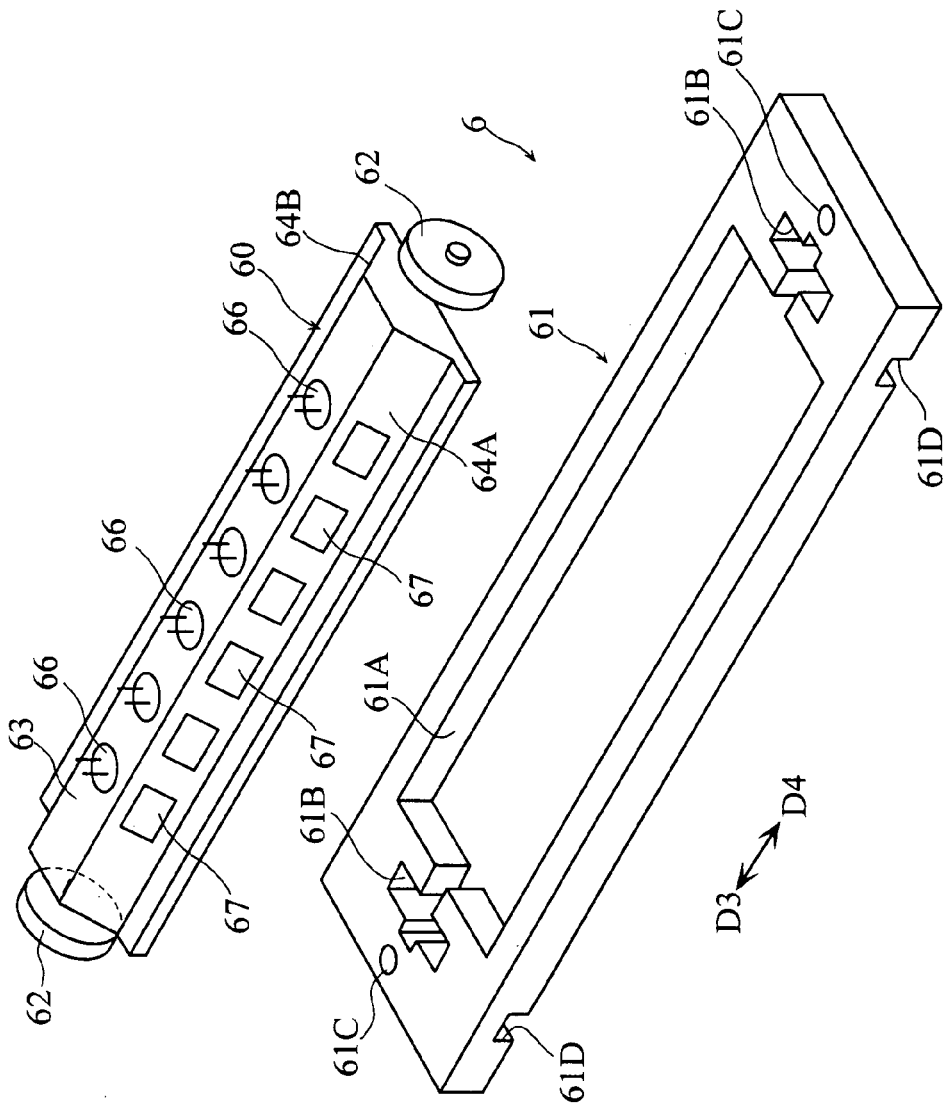

ANALYZER, METHOD FOR CLEANING PHOTOMETRY MECHANISM IN SUCH ANALYZER, AND CLEANING TOOL

TECHNICAL FIELD

The present invention relates to a technique for cleaning a photometry mechanism in an analyzer for analyzing a sample by an optical method using the photometry mechanism.

BACKGROUND ART

As shown in FIGS. 17 and 18, in an analyzer 9, for example, a test piece 92 placed at a placing portion 91 of a table 90 is transferred to a photometry mechanism 93 so that the sample is analyzed based on the measurements by the photometry mechanism 93 (see Patent Document 1, for example). The photometry mechanism 93 includes light emitting elements 95 and light receiving elements 96 held by a case 94. The case 94 includes a lower opening 97 covered by a transparent plate 98.

The light emitted from the light emitting elements 95 and the light reflected at a reagent pad 99 of the test piece 92 are supposed to pass through the transparent plate 98. However, when the surface 98a of the transparent plate 98 is dirty, the light is absorbed or reflected at the transparent plate 98. In light of this, it is desirable to frequently clean the surface 98a of the transparent plate 98.

In the analyzer 9, to prevent the light receiving elements 96 from receiving external light, the distance between the upper surface 90a of the table 90 and the surface 98a of the transparent plate 98 of the photometry mechanism 93 is set to be small, and the photometry mechanism 93 is located at a back portion of the analyzer. In such an arrangement, the cleaning of the transparent plate 98 is performed, with the clearance between the photometry mechanism 93 and the table 93 being lit with a flashlight, by inserting a cotton swab wet with a cleaning liquid into the clearance and rubbing the transparent plate 98 with the swab. As readily seen, the cleaning of the transparent plate 98 is not easy. Accordingly, the user may neglect the cleaning of the transparent plate 98, thinking of the difficulty of the operation. As a result, the reliability of the analysis deteriorates. Further, since the transparent plate 98 is not within easy access and the cleaning is performed manually, it depends on users how well the cleaning is finished. Unfavorably this dependency results in the difference in the analysis accuracy.
Patent Document 1: Japanese patent No. 2561509

DISCLOSURE OF THE INVENTION

Problems to be Solved by the Invention

An object of the present invention is to reduce the burden on the user in cleaning the photometry mechanism of an analyzer and to enhance the analysis accuracy.

Means for Solving the Problems

According to a first aspect of the present invention, there is provided an analyzer comprising: a photometry mechanism for photometrically analyzing a reagent pad of an analytical tool with a sample applied to the reagent pad; and a table including a placing portion at which the analytical tool is to be placed. The table supports a cleaning tool including a press portion. The photometry mechanism includes a light emitting surface or a light incident surface that is cleaned with the press portion being pressed against the light emitting surface or the light incident surface.

Preferably, the press portion of the cleaning tool is configured to rub the light emitting surface or the light incident surface of the photometry mechanism.

The photometry mechanism may be movable up and down relative to the table. The up and down movement of the photometry mechanism relative to the table may be achieved by making only the photometry mechanism movable up and down, making only the table movable up and down, or making both of the photometry mechanism and the table movable up and down.

Preferably, in the analyzer of the present invention, the light emitting surface or the light incident surface is cleaned with the cleaning tool placed at the placing portion. Preferably, in this case, when the cleaning tool is placed at the placing portion and the photometry mechanism is located at a position corresponding to the placing portion, the press portion of the cleaning tool is pressed against the light emitting surface or the light incident surface.

The table may include a guide extending in the movement direction of the table and including a recess. In this case, the photometry mechanism includes a contact portion for coming into contact with the guide, and the contact portion is received in the recess when the placing portion is located at a position where the photometrical analysis of the reagent pad is performed.

Preferably, in the analyzer of the present invention, the light emitting surface or the light incident surface of the photometry mechanism is heated when the press portion of the cleaning tool is impregnated with a cleaning liquid and pressed against the light emitting surface or the light incident surface.

In the analyzer of the present invention, the degree of dirtiness of the light emitting surface or the light incident surface of the photometry mechanism may be checked by utilizing a reference plate having a predetermined reflectance. Preferably, in this case, the checking of the degree of dirtiness of the light emitting surface or the light incident surface may be performed when the power source is turned on or immediately after the light emitting surface or the light incident surface is cleaned. As the reference plate, use may be made of one which is to be irradiated with light from a light source in checking the output of the power source of the photometry mechanism.

According to a second aspect of the present invention, there is provided a method for cleaning the light emitting surface or the light incident surface of the photometry mechanism in the analyzer according to the first aspect of the present invention. The cleaning method includes a first step of rubbing the light emitting surface or the light incident surface with a press portion of the cleaning tool, with the press portion impregnated with a cleaning liquid. The method further includes at least one of the second and the third steps below.

The second step, which is performed before the first step, comprises heating the light emitting surface or the light incident surface of the photometry mechanism, with the press portion impregnated with cleaning liquid and pressed against the light emitting surface or the light incident surface. The third step, which is performed after the first step, comprises checking the degree of dirtiness of the light emitting surface or the light incident surface utilizing a reference plate having a predetermined reflectance.

According to a third aspect of the present invention, there is provided a cleaning tool for an analyzer comprising a photometry mechanism and a table, wherein the photometry mechanism is configured to photometrically analyze a reagent pad of an analytical tool with a sample applied to the reagent pad, and the table includes a placing portion at which the analytical tool is placed. The cleaning tool is used for cleaning a light emitting surface or a light incident surface of the photometry mechanism. The cleaning tool comprises a base plate, and at least one press portion supported by the base plate.

The base plate may have a shape substantially similar to that of a substrate of the analytical tool that supports the reagent pad. The press portion is provided at least at a location corresponding to the reagent pad of the analytical tool. Preferably, the press portion has a shape similar to that of the reagent pad in plan view and is provided at a location corresponding to the reagent pad.

Preferably, the press portion is thicker than the reagent pad of the analytical tool. For instance, the thickness of the press portion may be 2 to 30 times the thickness of the reagent pad, and preferably, 3 to 20 times the thickness of the reagent pad.

Preferably, the press portion has at least either of elasticity and water absorbency. To make the press portion elastic, part or the entirety of the press portion may be made of non-porous material such as rubber. To make the press portion water-absorbent, part or the entirety of the press portion may be made of a cloth made of a highly water-absorbent material such as cotton yarn or a cloth made of ultrafine fiber such as dividing thread. To make the press portion elastic and water-absorbent, the press portion may be made of a combination of an elastic material and a water-absorbent material or entirely made of a porous material such as expanded resin (sponge).

The press portion may comprise an elastic layer and a water-absorbent layer laminated on the elastic layer. In this case, the elastic layer may be made of silicone rubber or silicone sponge, whereas the water-absorbent layer may be made of cloth made of dividing thread (ultrafine fiber) of nylon and polyester, non-woven fabric made of resin such as polyester, nylon or rayon, or non-woven fabric obtained by bonding a web made of the exemplified resin with a resin such as acrylic-based resin.

The press portion may not be in the form of a pad. For instance, the press portion may be in the form of a brush made of a plurality of linear strips or may be in the form of a strip extending wider than the reagent pad.

BRIEF DESCRIPTION OF THE DRAWINGS

FIG. 5A is an overall perspective view of a cleaning tool used in the analyzer shown in FIG. 1, whereas

FIG. 7 is an exploded perspective view of the photometry mechanism shown in FIG. 6.

FIG. 8A is a sectional view taken along lines VIIIa-VIIIa in FIG. 6, whereas

DESCRIPTION OF REFERENCE SIGNS

1 Analyzer
20, 21 Test piece (analytical tool)
20A, 21A Substrate (of test piece)
20B, 21B Reagent pad (of test piece)
22 Cleaning tool
22A Base plate (of cleaning tool)
22B Cleaning pad (press portion) (of cleaning tool)
22Ba Elastic layer (of cleaning pad)
22Bb Water-absorbent layer (of cleaning pad)
4 Test piece table (table)
41 First slit (placing portion) (of test piece table)
43 Guide portion (guide)
43Bb Second recess (recess) (of guide portion)
45A Black reference plate (reference plate)
45B White reference plate (reference plate)
6 Photometry mechanism
62 Roller (contact portion) (of photometry mechanism)
68 Transparent plate (a member including a light emitting surface and a light incident surface) (of photometry mechanism)

BEST MODE FOR CARRYING OUT THE INVENTION

Figure 1:
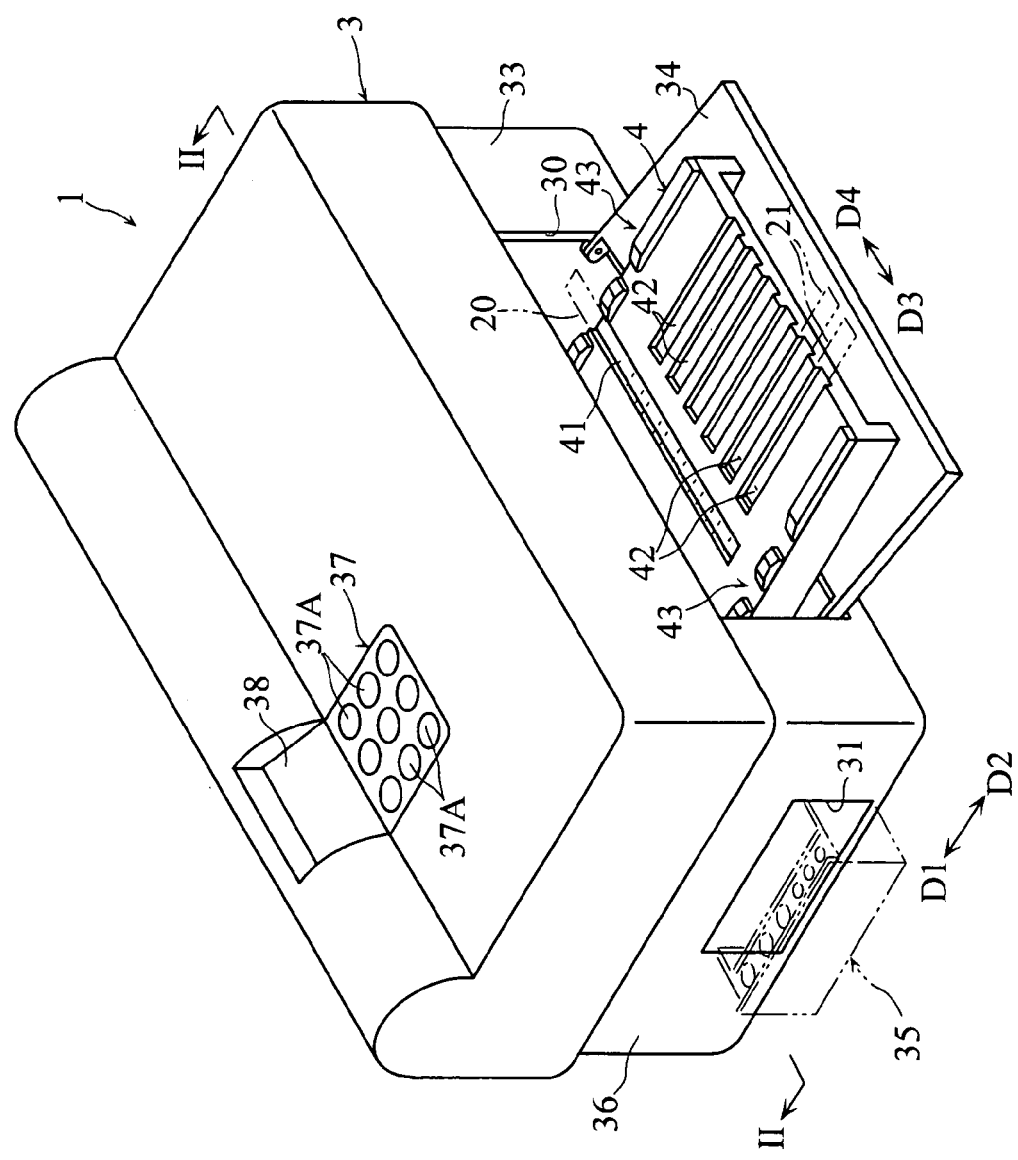
FIG. 1 is an overall perspective view showing an example of analyzer according to the present invention.
Figure 2:
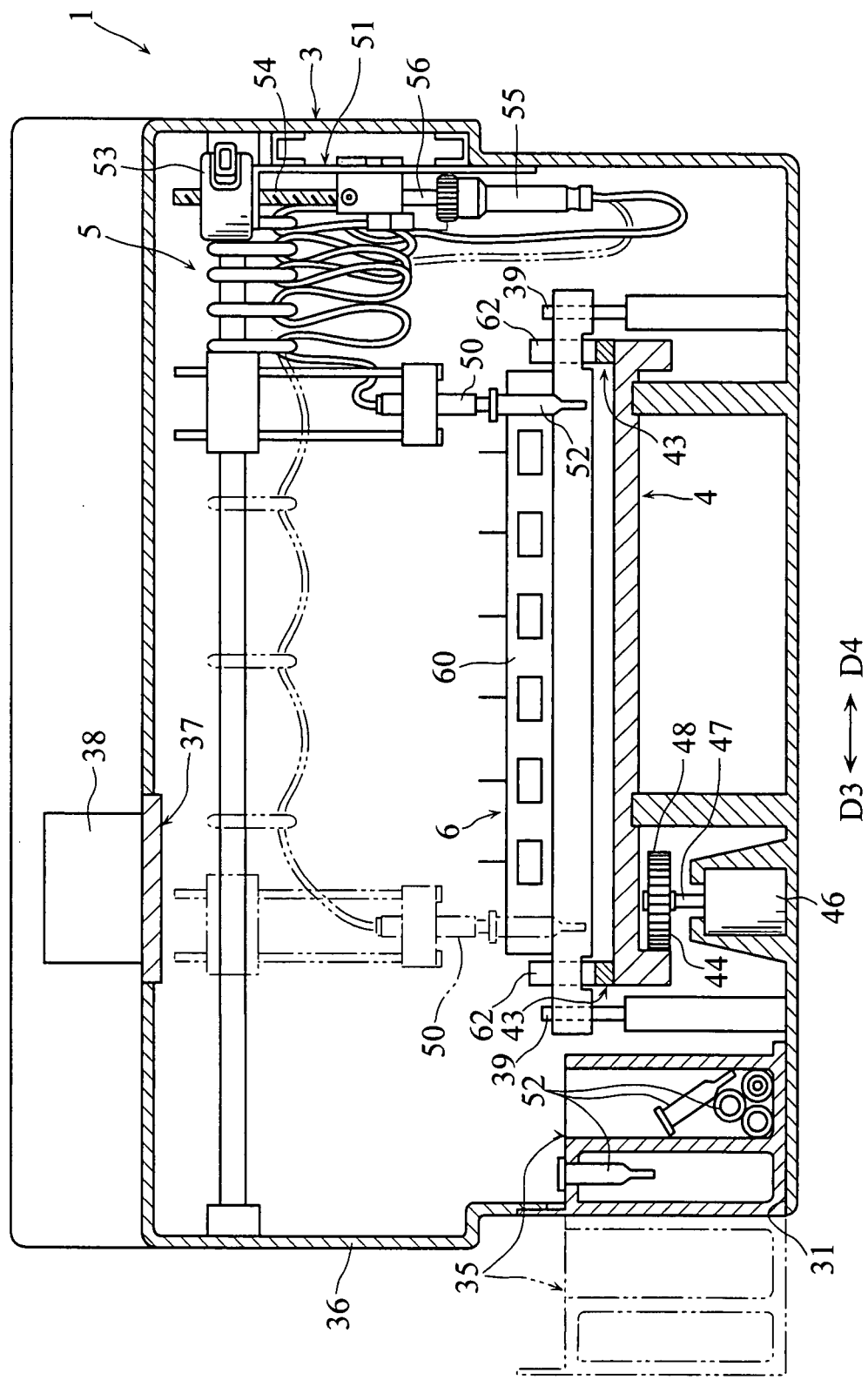
FIG. 2 is a sectional view taken along lines II-II in FIG. 1.

The analyzer 1 shown in FIGS. 1 and 2 analyzes the concentration of a particular component in blood using test pieces 20 and 21. The analyzer includes a housing 3, a test piece table 4, a dispenser 5 and a photometry mechanism 6.

The housing 3 defines the outer shape of the analyzer 1, accommodates various elements, and is formed with openings 30 and 31:

The opening 30 allows the test piece table 4 to partially project from the housing 3 and is provided at a front surface 33 of the housing 3. The opening 30 is selectively opened or closed by a lid 34. When the opening 30 is in the open state, the inside and outside of the housing 3 communicate with each other, whereby it is possible to select one from the two states, i.e. a state in which the test piece table 4 is accommodated in the housing 3 and another state in which most part of the test piece table 4 projects from the housing 3. When the test piece table 4 projects from the housing 3, the first slit 41 and the second slits 42 of the test piece table 4, which will be described later, are exposed.

The other opening 31 is utilized for taking a rack 35 out of the housing 3 and back into it. The opening 31 is provided at a side surface 36 of the housing 3 and is selectively opened or closed by the rack 35. The rack 35 is utilized for holding tips 52 and containers (not shown) containing a sample or a cleaning liquid. The rack is also utilized for storing used tips 52.

The housing 3 is further provided with an operation panel 37 and a display 38. The operation panel 37 includes various operation buttons 37A for setting measurement conditions or controlling the operation of the analyzer 1. The display 38 displays e.g. the measurements, the results of operation of the control buttons 37A or information such as error message.

Figure 3:
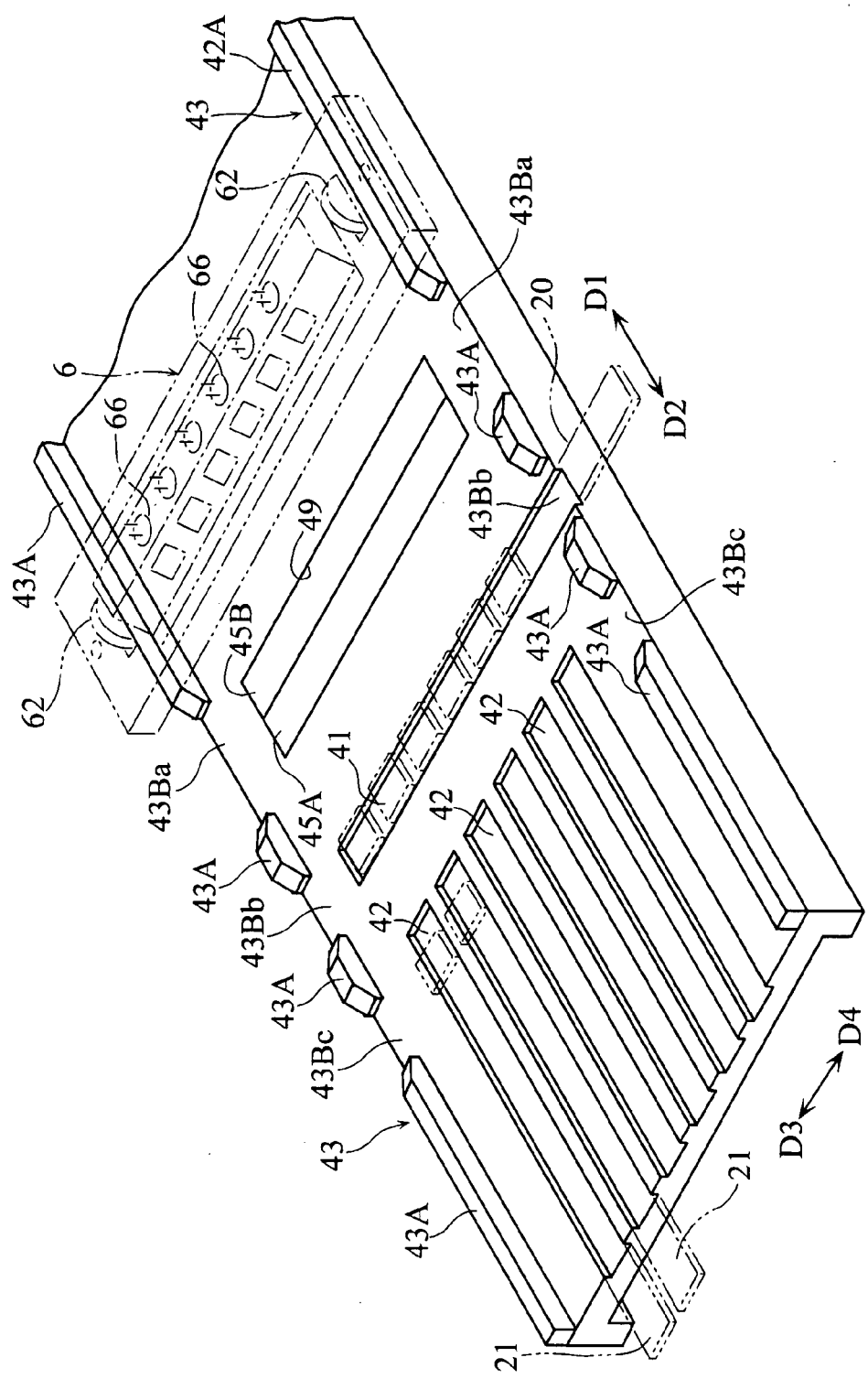
FIG. 3 is a perspective view showing a table of the analyzer shown in FIG. 1.

As shown in FIGS. 1 and 3, the test piece table 4 is used for placing the test pieces 20 and 21 and moving the test pieces 20 and 21 to an intended position. The test piece table is reciprocally movable in the directions D1, D2 relative to the housing 3. The test piece table 4 includes a first slit 41, a plurality of second slits 42 (six in this embodiment), a pair of guide portions 43, a gear 44, and a black and a white reference plates 45A and 45B. The test piece table 4 may be entirely black.

Figure 4A:
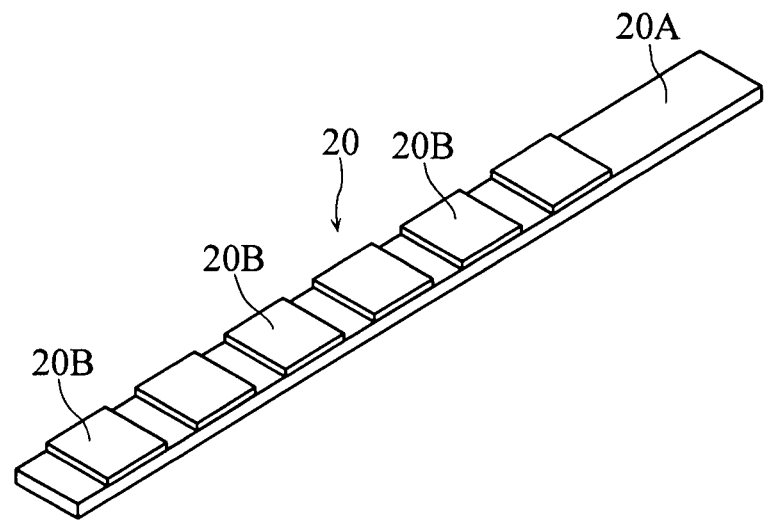
FIG. 4 includes an overall perspective view showing a test piece used for the analyzer shown in FIG. 1.
Figure 5A:
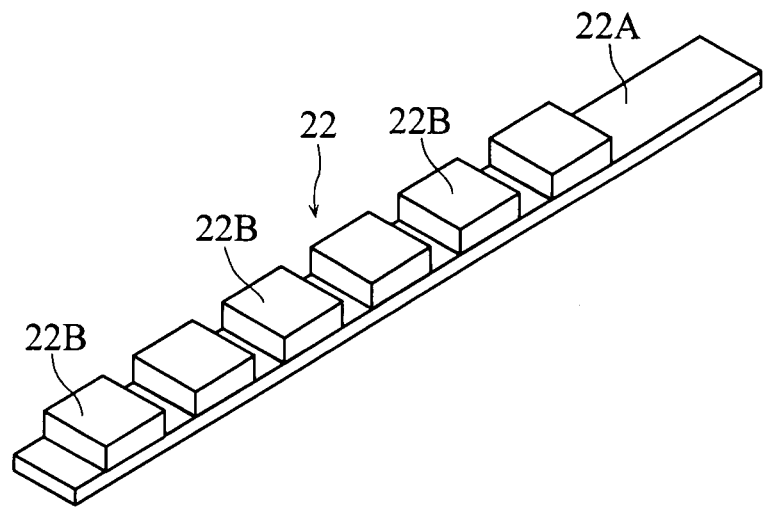

The first slit 41 holds a test piece 20 for multi-component measurement shown in FIG. 4A or a cleaning tool 22 shown in FIG. 5A. The first slit 41 extends in the directions D3, D4.

As shown in FIG. 4A, the test piece 20 for multi-component measurement includes a substrate 20A and a plurality of reagent pads 20B (six reagent pads in this embodiment) provided on the substrate. The substrate 20A may be made of a non-water-absorbent or almost non-water-absorbent resin into a shape corresponding to that of the first slit 41. Each of the reagent pads 20B may comprise a water-absorbent carrier, such as woven fabric or filter paper, carrying a reagent which develops color upon reaction with a particular component such as glucose, albumin or calcium.

The cleaning tool 22 shown in FIG. 5A cleans the transparent plate 68 (see FIG. 8B) of the photometry mechanism 6, which will be described later. The cleaning tool 22 includes a base plate 22A and six cleaning pads 22B provided on the base plate. Similarly to the test piece 20, the base plate 22A may be made of a non-water-absorbent or almost non-water-absorbent resin into a shape corresponding to that of the first slit 41. The cleaning pads 22 are arranged at locations corresponding to the reagent pads 20B of the test piece 20 and have a thickness larger than that of the reagent pads 20B. The thickness of each cleaning pad 22B may be about 2 to 30 times that of the reagent pads 20, and preferably, 3 to 20 times that of the reagent pads 20. When the thickness of the cleaning pads 22B is too small, the cleaning pads cannot be sufficiently pressed against the transparent plate 68 (see FIG. 8B) of the photometry mechanism 8, and hence, sufficient cleaning will not result. When the thickness of the cleaning pads 22B is too large, an excessively large pressing force is applied to the transparent plate 68 (see FIG. 8B) of the photometry mechanism 8. In this case, the transparent plate 68 may be damaged or it may be difficult to move (rub) the cleaning pads 22B (cleaning tool 22) relative to the transparent plate 68.

The cleaning pads 22 are elastic and water-absorbent. The cleaning pad 22 may be comprise a single layer which is elastic and water-absorbent or have a two-layer structure comprising an elastic layer 22Ba and a water-absorbent layer 22Bb laminated on the elastic layer. The elastic layer 22Ba may also have water absorbency in addition to the elasticity.

To make the cleaning pad 22B of a single-layer structure, use may be made of cotton, expanded resin (sponge) or knitted fabric for the material. To make the cleaning pad 22B of a double-layer structure, use may be made of elastomer such as silicone rubber or expanded resin such as silicone sponge for the material of the elastic layer 22Ba, and filter paper, woven fabric or non-woven fabric for the material of the water-absorbent layer 22Bb. Specifically, the water-absorbent layer 22Bb may be made of cloth using ultrafine fiber which is a dividing thread of polyester and nylon, non-woven fabric made of resin such as polyester, nylon or rayon, or non-woven fabric obtained by bonding a web made of the exemplified resin with a resin such as acrylic-based resin. The cleaning pad 22B may carry a surface-active agent such as Triton X-100 (polyoxyethylene p-t-octylphenyl ether).

Figure 4B:
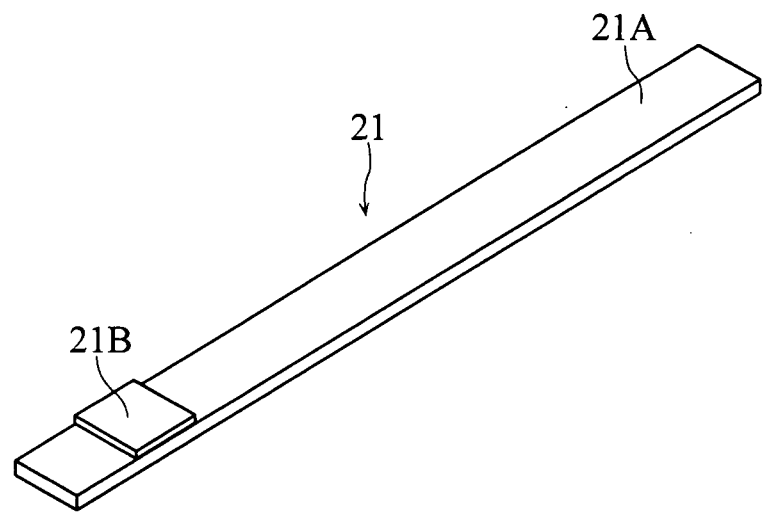

Each of the second slits 42 shown in FIGS. 1 and 3 is utilized for holding a test piece 21 for single-component measurement and extends in the directions D1, D2. As shown in FIG. 4B, the test piece 21 for single-component measurement includes a substrate 21A and a single reagent pad 21B provided on the substrate. The reagent pad 21B may comprise a water-absorbent carrier such as woven fabric or filter paper carrying a reagent which develops color upon reaction with a particular component such as glucose, albumin or calcium.

As shown in FIG. 3, each of the guide portions 43 guides the rolling of a roller 62 of the photometry mechanism 6, which will be described later, when the test piece table 4 moves in the directions D1, D2 (see FIGS. 11, 13, 14 and 16). The guide portions 43 extend in the directions D1, D2 at opposite ends of the test piece table 4 in the directions of D3, D4. Each of the guide portions 43 includes a first through a third recesses 43Ba, 43Bb and 43Bc defined by a plurality of rails 43A. The first recess 43Ba is provided at a location corresponding to the black and the white reference plates 45A and 45B. The second recess 43Bb is provided at a location corresponding to the first slit 41. The third recess 43Bc is provided at a location corresponding to the second slits 42.

As shown in FIG. 2, the gear 44 transmits the rotational driving force of the motor 46 to the test piece table 4. The gear 44 includes a plurality of teeth (not shown) for meshing with a gear 48 fixed to an output shaft 47 of the motor 46. Thus, the test piece table 4 moves relative to the housing 3 reciprocally in the direction D1 or D2 (see FIGS. 1 and 3) in accordance with the rotation direction of the output shaft 47 of the motor 46.

The black and the white reference plates 45A and 45B shown in FIG. 3 are irradiated with light from the light emitting elements 66 in measuring the output from the light emitting elements 66 of the photometry mechanism 6, which will be described later, or in checking the cleaning state of the transparent plate 68 of the photometry mechanism 6. The reference plates 45A and 45B have predetermined reflectance and may be made of glass or resin. Each of the reference plates 45A and 45B is fitted in a recess 49 formed at the test piece table 4 to be integral with the test piece table 4. It is to be noted that one of the black reference plate 45A and the white reference plate 45B may be omitted. Further, when the test piece table 4 is black, the surface of the test piece table 4 may be utilized instead of the black reference plate 45A. Instead of the white reference plate 45B, use may be made of a reference plate made of a material having a high reflectance at the surface (e.g. metal).

Figure 5B:
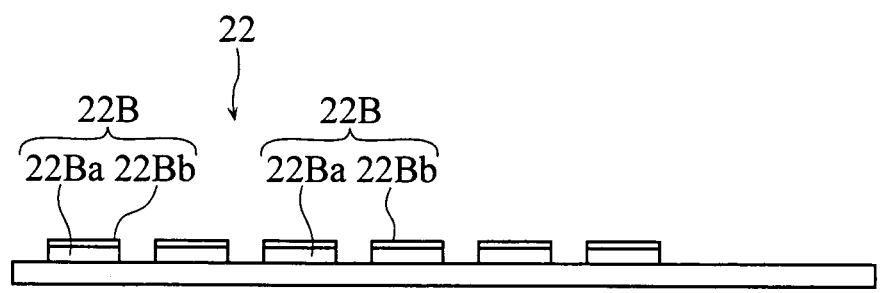
FIG. 5B is a side view of the cleaning tool.

The dispenser 5 shown in FIG. 2 applies a sample to the reagent pads 20B, 21B of the test pieces 20, 21 shown in FIGS. 4A and 4B or applies a cleaning liquid to the cleaning pads 22B of the cleaning tool 22 shown in FIG. 5A or 5B. Examples of sample to be analyzed by the analyzer 1 are blood and urine. As the cleaning liquid, use may be made of a solution containing water, an organic solvent and a surface-active agent. However, when the cleaning pads 22B of the cleaning tool 22 are impregnated with a surface-active agent, it is not necessary to use a solution containing a surface-active agent as the cleaning liquid.

The dispenser 5 includes a nozzle 50 and a pump unit 51. The pump unit 51 applies suction force or discharging force to the nozzle 50.

The nozzle 50 shown in FIG. 2 is used with a tip 52 mounted to the end thereof and movable horizontally and vertically. By utilizing the motive power from the pump unit 51, the nozzle 50 selectively sucks or discharges air. Specifically, with the tip 52 mounted to the nozzle 50, the nozzle 50 is capable of sucking air to suck the sample and retain the sample in the tip 52 and discharging air to discharge the sample from the tip 52.

The pump unit 51 is designed to move up and down a direct-acting shaft 54 by a pulse motor 53. The direct-acting shaft 54 is connected to a piston 56, and the piston 56 moves up and down relative to a syringe 55 in accordance with the up-down movement of the direct-acting shaft 54. In this way, by controlling the pulse motor 53, the pump unit 51 moves up and down the piston 56 to suck liquid into the tip 52 attached to the nozzle 50 or discharge liquid from the tip 52.

Figure 6:
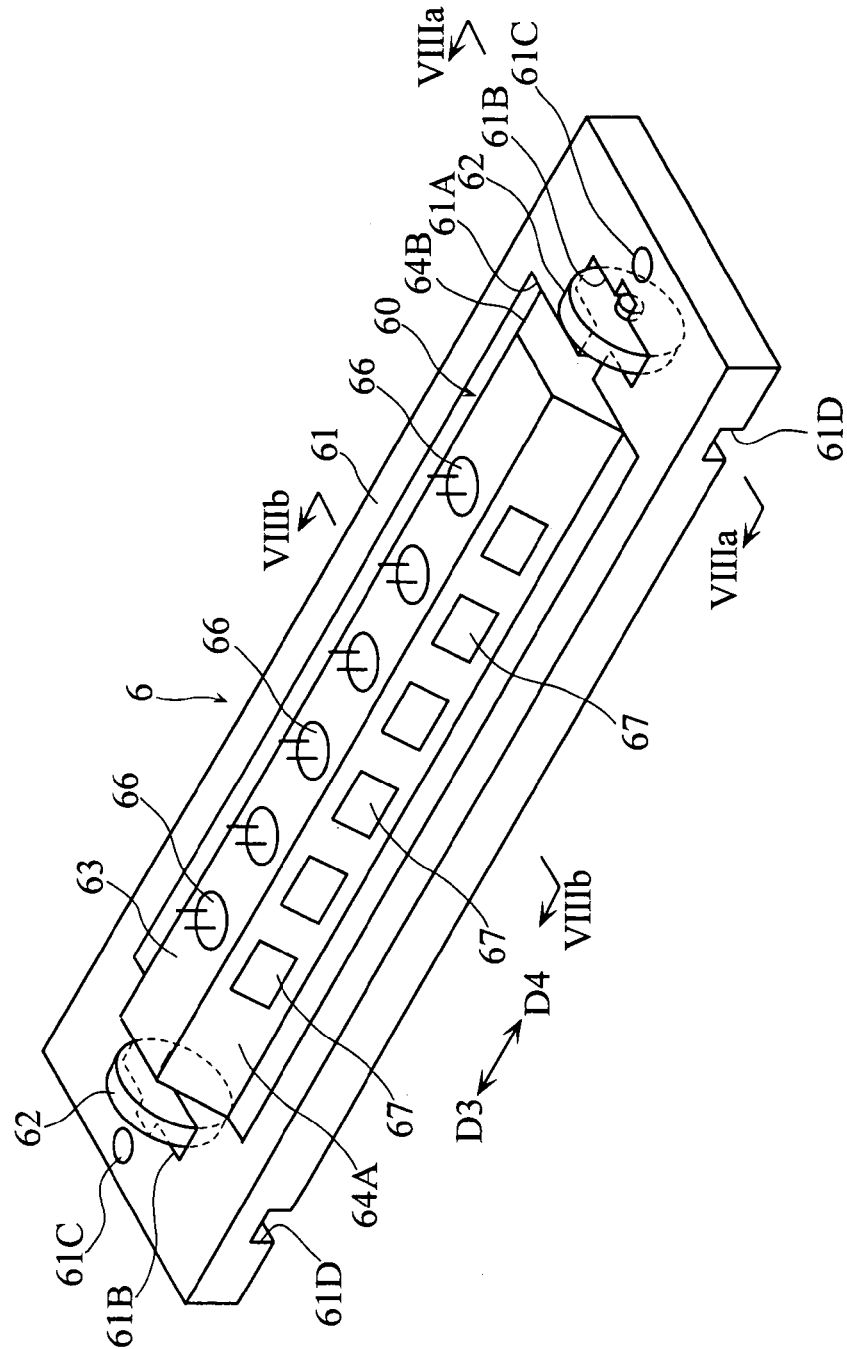
FIG. 6 is an overall perspective view of a photometry mechanism of the analyzer shown in FIG. 1.
Figure 8A:
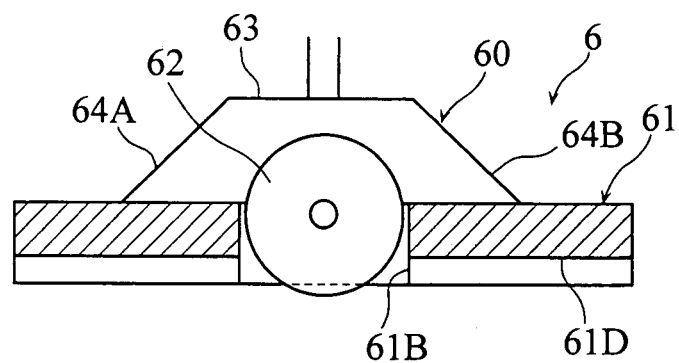
Figure 8B:
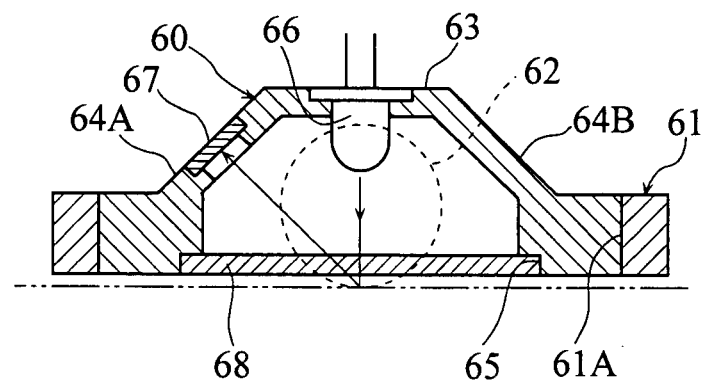
FIG. 8B is a sectional view taken along lines VIIIb-VIIIb in FIG. 6.

The photometry mechanism 6 shown in FIG. 2 serves to grasp the degree of color development at the reagent pads 20B, 21B (see FIG. 1) of the test pieces 20, 21. As shown in FIGS. 6-8, the photometry mechanism 6 includes a case 60, a holder 61 and a pair of rollers 62.

The case 60 is entirely elongated in the directions D3, D4 and includes an upper wall 63, a pair of inclined walls 64A, 64B and a lower opening 65.

The upper wall 63 extends horizontally in the directions D3, D4 and supports a plurality of light emitting elements 66 (six in the figure) aligned in the directions D3, D4. The light emitting elements 66 are arranged correspondingly to the arrangement of the reagent pads 20B of the test piece 20. Each of the light emitting elements 66 is so supported as to emit light vertically downward to vertically illuminate the reagent pads 20B, 21B of the test pieces 20, 21 or the reference plates 45A, 45B (see FIGS. 8B and 11B). As the light emitting elements 66, use may be made of LED lamps.

Each of the inclined walls 64A and 64B is inclined 45 degrees with respect to the upper wall 63 and extends in the directions D3, D4. The inclined wall 64A supports a plurality of light receiving elements 67 (six in the figure). The light receiving elements 67 are so supported that, of the light rays reflected at the reagent pads 20B, 21B of the test pieces 20, 21 or the reference plates 45A, 45B, the light rays reflected at 45 degrees are received by the light receiving elements (see FIGS. 8B and 11B). As the light receiving elements 67, use may be made of photodiodes.

The lower opening 65 allows the light emitted from the light emitting elements 66 to exit the case 60 and allows the light reflected at the reagent pads 20B, 21B of the test pieces 20, 21 to enter the case 60. The transparent plate 68 is fixed to the lower opening 65. The transparent plate 68 may be made of a transparent resin or glass.

The holder 61 makes it possible for the photometry mechanism 6 including the case 60 to move up and down. The holder includes a through-hole 61A for holding the case 60. The holder 61 further includes openings 61B, 61C and grooves 61D at opposite ends in the directions D3, D4. The openings 61B allow the rotation of the rollers 62. As shown in FIG. 2, the openings 61C receive pins 39, and the pins 39 guide the up-down movement of the photometry mechanism 6. The grooves 61D are provided to prevent the holder 61 from coming into contact with the guide portions 43 of the test piece table 4 when the photometry mechanism 6 is moved downward.

As shown in FIGS. 2, 6 and 8, the paired rollers 62 are supported rotatably relative to the case 60 at opposite ends of the case 60 in the longitudinal direction (directions D3, D4) while partially projecting downward from the holder 61. Each of the rollers 62 is provided at a location corresponding to the guide portion 43 (see FIG. 3) of the test piece table 4 so that the roller 62 rotates on the guide portion 43 when the test piece table 4 moves in the directions D1, D2 relative to the photometry mechanism 6. As noted before, each guide portion 43 includes a first through a third recesses 43Ba, 43Bb and 43Bc. Therefore, when the roller 62 is located on the rail 43A, the entirety of the photometry mechanism 6 is located at a higher position. When the roller 62 is located in the recess 43Ba-43Bc, the entirety of the photometry mechanism 6 is located at a lower position. In this way, by the relative movement of the rollers 62 along the guide portions 43 in the directions D1, D2, the photometry mechanism 6 moves up and down and is located at a lower position when the photometry mechanism comes to a position corresponding to the black and the white reference plates 45A, 45B or a position corresponding to the first slit 41 or the second slits 42.

Figure 13A:
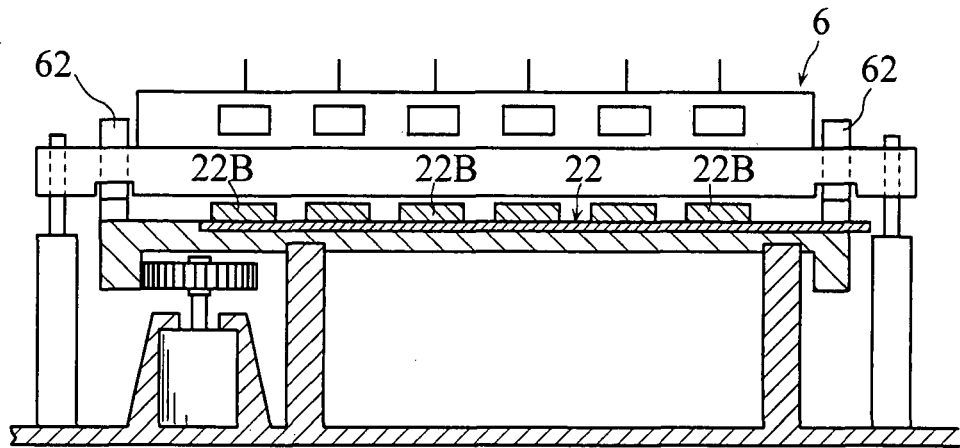
FIG. 13 includes a sectional view of a principal portion for describing the operation of the analyzer in the cleaning process.
Figure 13B:
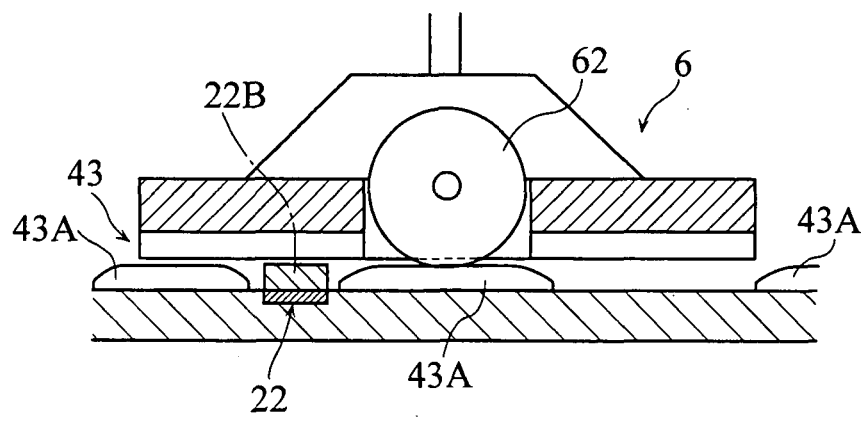
Figure 13C:
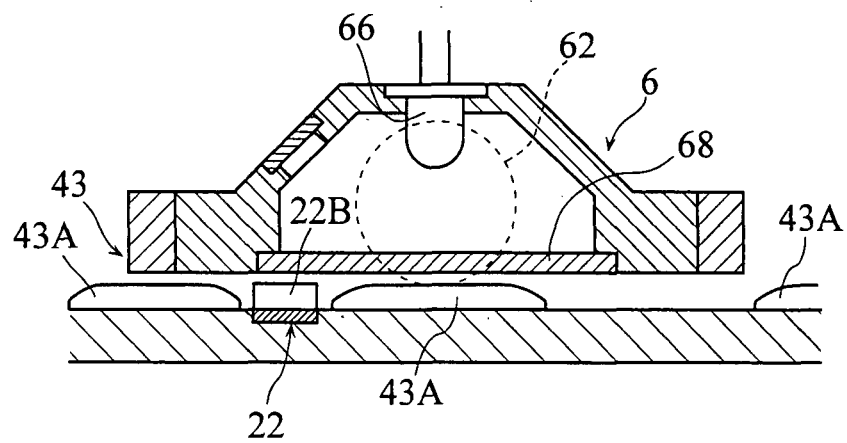

The height of the rails 43A is so set that, when the rollers 62 are located on the rails 43A, the surface of the transparent plate 68 of the photometry mechanism 6 is positioned higher than the upper surface of the cleaning pads 22B of the cleaning tool 22 placed at the first slit 41 (see FIGS. 13B and 13C). Further, the height of the rails 43A is so set that, when the rollers 62 are located at the first through the third recesses 43Ba-43Bc, the surface of the transparent plate 68 is positioned lower than the upper surface of the cleaning pads 22B of the cleaning tool 22 placed at the first slit 41 and higher than the upper surface of the reagent pads 20B, 21B of the test pieces 20, 21 placed at the first and the second slits 41, 42 (see FIGS. 14C and 16).

The operation of the analyzer 1 will be described below with reference to flowcharts.

Figure 9:
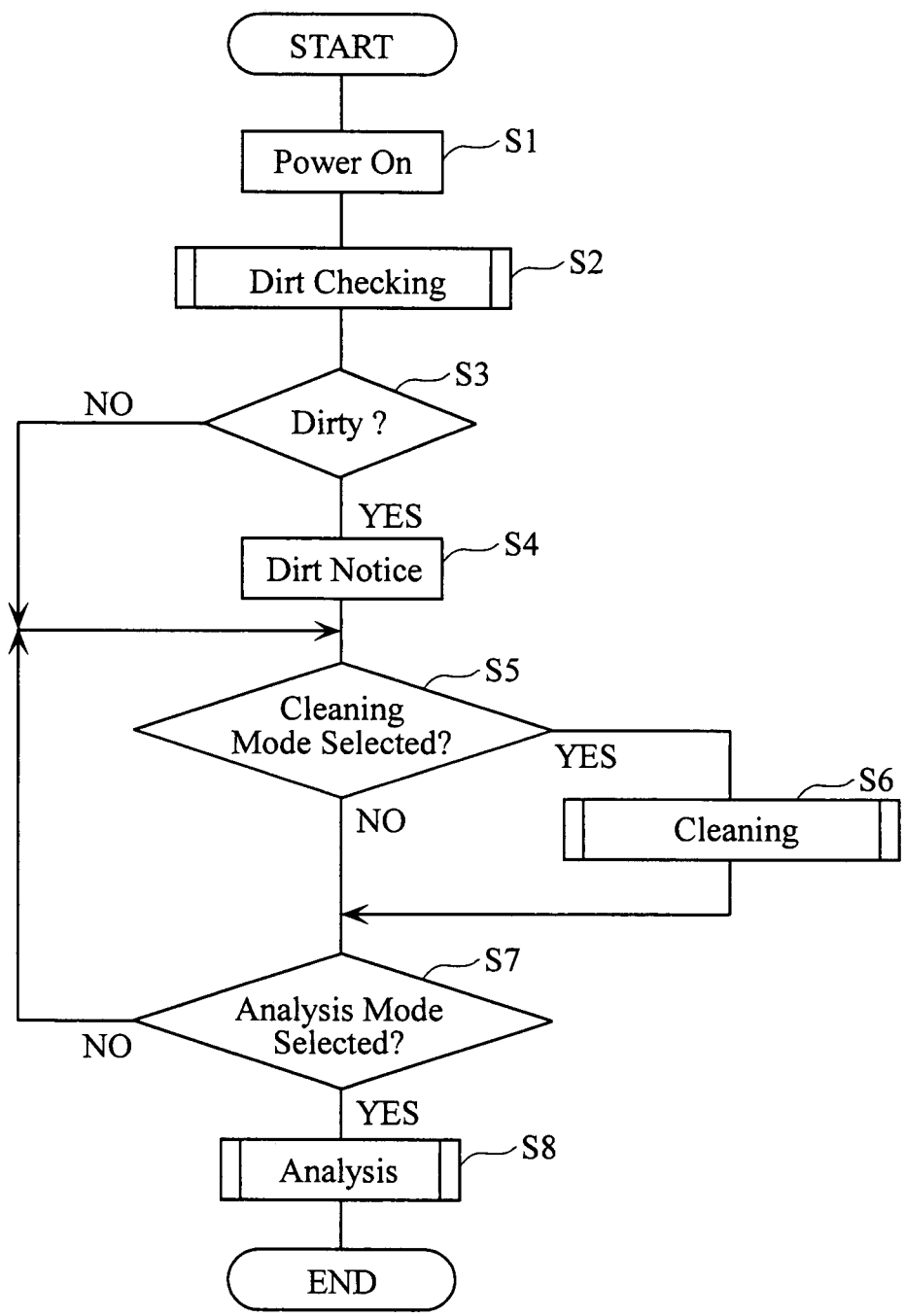
FIG. 9 is a flowchart for describing the operation of the analyzer shown in FIG. 1.

As shown in FIG. 9, in the analyzer 1, when the power source is turned on (S1), it is checked whether or not the transparent plate 68 of the photometry mechanism 6 is dirty (S2).

Figure 10:
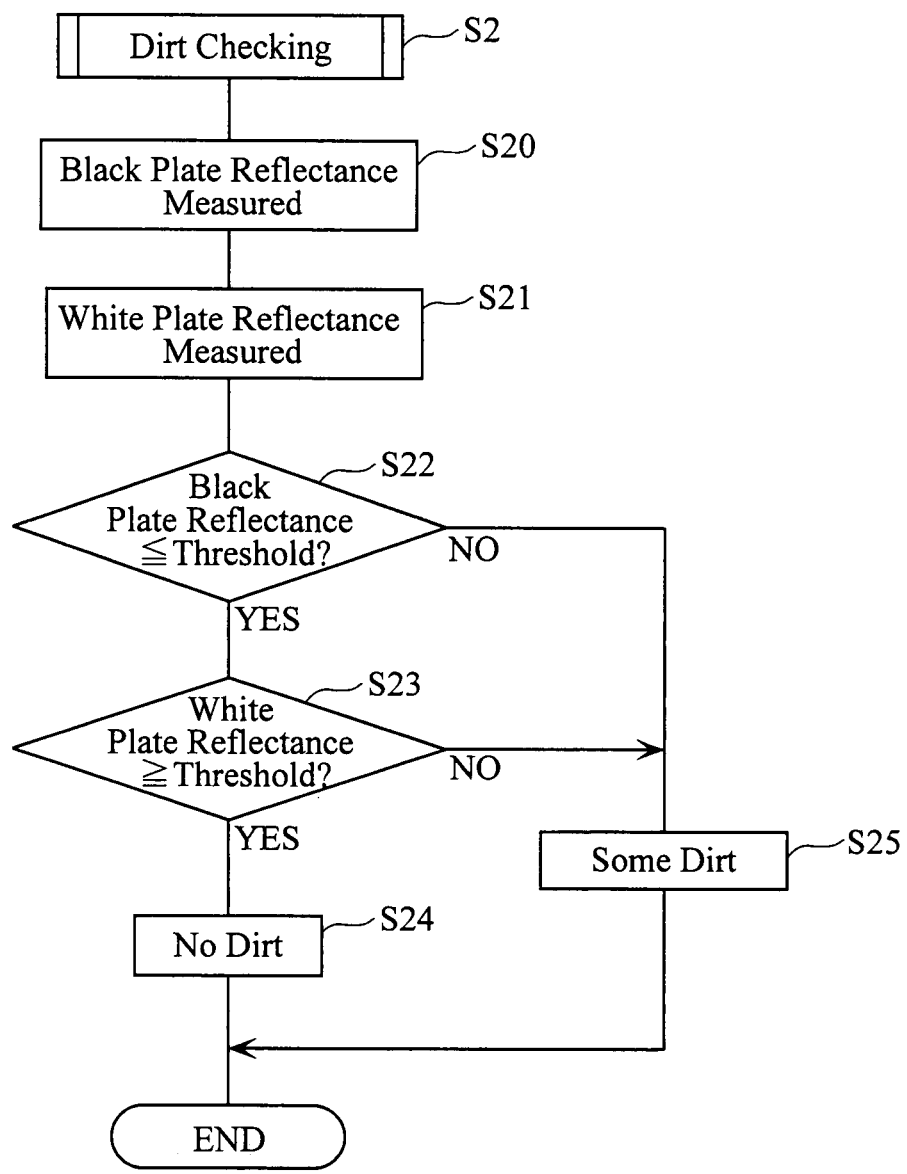
FIG. 10 is a flowchart for describing the dirt checking process of the analyzer shown in FIG. 1.
Figure 11A:
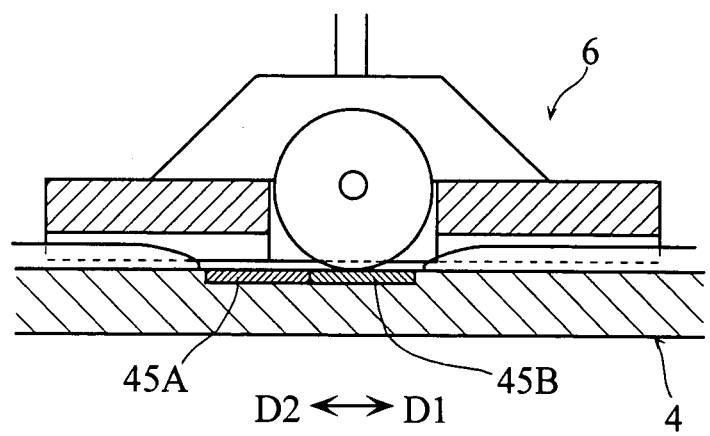
FIG. 11 includes a sectional view of a principal portion for describing the operation of the analyzer in the dirt checking process.
Figure 11B:
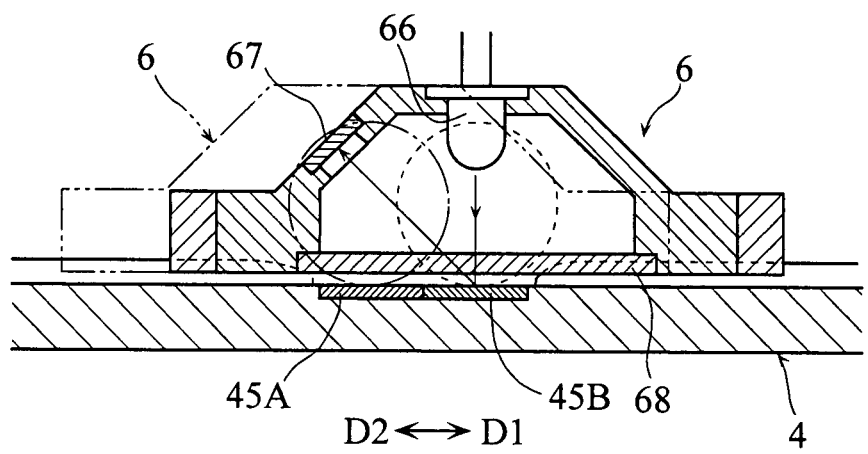

As shown in FIG. 10, in the process step to check the transparent plate 68 for dirt (S2), the analyzer 1 measures the reflectance of the black reference plate 45A and the white reference plate 45B (S20, S21). As shown in FIGS. 11A and 11B, the measurement of reflectance at the black and the white reference plates 45A and 45B (S20, S21) is performed by positioning the photometry mechanism 6 at a location corresponding to the black and the white reference plates 45A and 45B and then performing photometry with respect to the reference plates 45A, 45B by the photometry mechanism 6. The photometry of the reference plates 45A and 45B is performed by irradiating the reference plates 45A and 45B with light from the light emitting elements 66 and receiving the reflected light at the light receiving elements 67. In the analyzer 1, the reflectance of the reference plates 45A and 45B is computed based on the amount of light received at the light receiving elements 67.

Then, in the analyzer 1, whether or not the reflectance of the black reference plate 45A is not higher than a predetermined value is determined (S22). When the reflectance is equal to or below the predetermined value (S22: YES), it is determined whether or not the reflectance of the white reference plate 45B is not lower than a predetermined value (S23). When the reflectance of the white reference plate 45B is equal to or above the predetermined value in S23, the analyzer 1 determines that there is no dirt on the transparent plate 68 (S24). When the reflectance of the black reference plate 45A is higher than the predetermined value in S22 (S22: NO) or the reflectance of the white reference plate 45B is lower than the predetermined value in S23 (S23: NO), the transparent plate 68 is determined to be dirty (S25).

The thresholds for the reflectance of the black and the white reference plates 45A and 45B, which is utilized as the basis for determining whether the transparent plate 68 is dirty or not, may be set in light of the wavelength of the irradiating light and the reflectance of the black and white reference plates 45A, 45B when they are clean (and further the composition of the reference plates 45A and 45B, etc.).

As shown in FIG. 9, after the checking of the transparent plate 68 for dirt (S2) is completed, the analyzer 1 determines whether there is dirt on the transparent plate 68 or not (S3). When it is determined that there is dirt on the transparent plate 68 (S2: YES), the analyzer gives notice that the transparent plate 68 is dirty (S4).

When it is determined that there is no dirt on the transparent plate 68 (S3: NO) or when notice is given that the transparent plate 68 is dirty (S4), the analyzer 1 determines whether or not the cleaning mode is selected by the user (S5). The selection of the cleaning mode may be performed by operating the operation buttons 37A by the user.

When it is determined that the cleaning mode is selected (S5: YES), the analyzer 1 performs the cleaning (S6).

Figure 12:
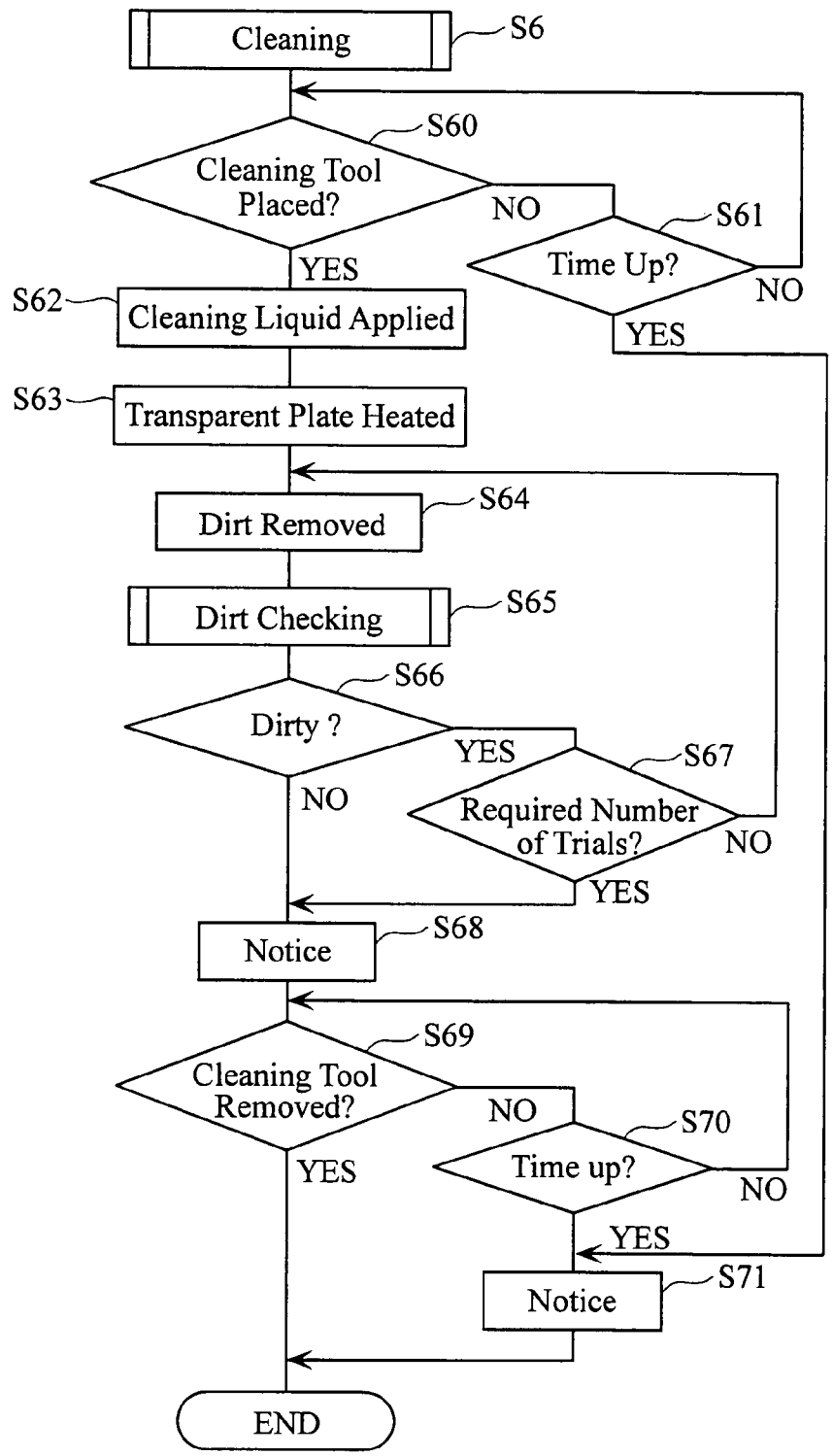
FIG. 12 is a flowchart for describing the cleaning process of the analyzer shown in FIG. 1.

As shown in FIG. 12, in the cleaning process (S6), it is first determined whether or not the cleaning tool 22 is placed at the first slit 41 (S60). When it is determined in S60 that the cleaning tool 22 is not plated (S60: NO), whether or not a predetermined time has elapsed (time up or not) after the selection of the cleaning mode is determined (S61). When the analyzer 1 determines that the predetermined time has not elapsed (S61: NO), whether or not the cleaning tool 22 is placed is determined again (S60). The determination of S60 and S61 is repeated until it is determined in S60 that the cleaning tool 22 is placed (S60: YES) or it is determined in S61 that the predetermined time has elapsed (time up) (S61: YES).

When it is determined in S60 that the cleaning tool 22 is placed (S60: YES), a cleaning liquid (e.g. water, solution of a surface-active agent or solvent) is applied to the cleaning pads 22B of the cleaning tool 22 (S62). The application of the cleaning liquid to the cleaning pads 22B is performed by sucking the cleaning liquid into the tip 52 attached to the nozzle 50 of the dispenser 5 and then discharging the cleaning liquid onto the cleaning pads 22 (see FIG. 2). Since the cleaning pads 22B are water-absorbent as noted before, the cleaning liquid applied to the cleaning pads 22 is retained in the cleaning pads 22B.

After the application of the cleaning liquid to the cleaning pads 22B (S62) is completed, the test piece table 4 is moved to bring the cleaning pads 22B into close contact with the transparent plate 68 of the photometry mechanism 6 (S63).

Figure 14A:
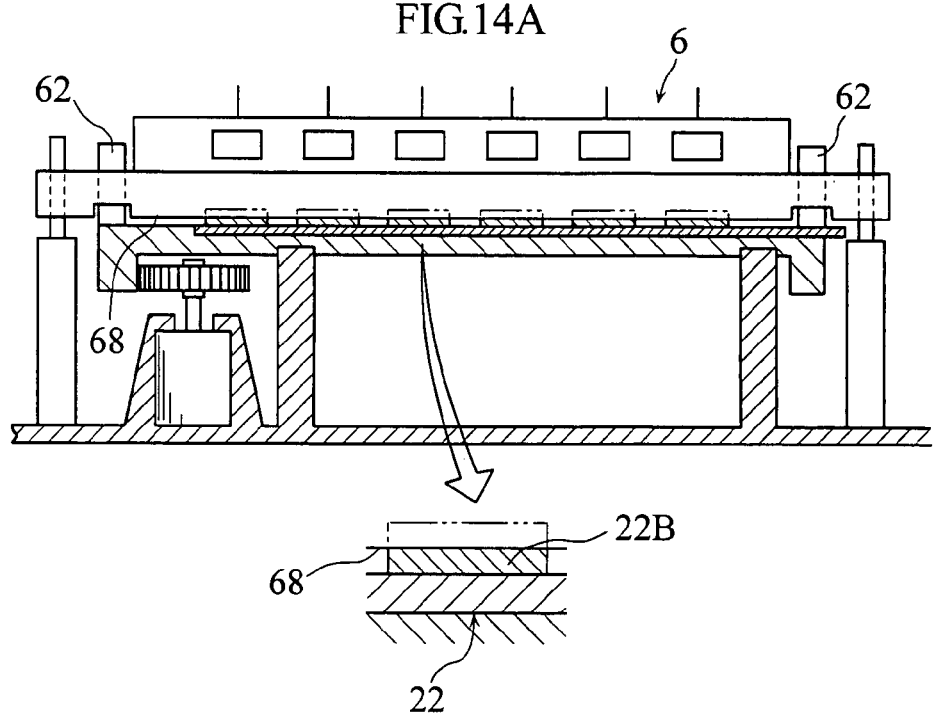
FIG. 14 includes a sectional view of a principal portion for describing the operation of the analyzer in the cleaning process.
Figure 14B:
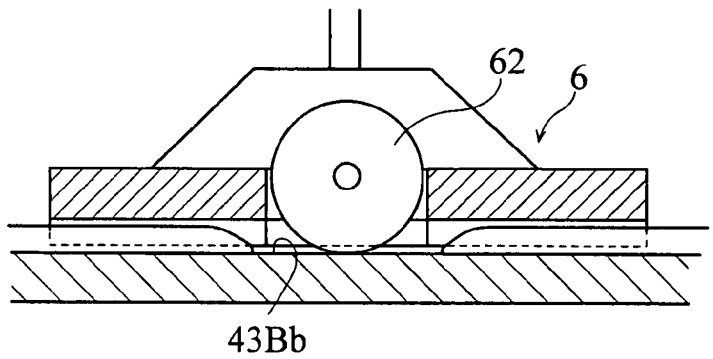
Figure 14C:
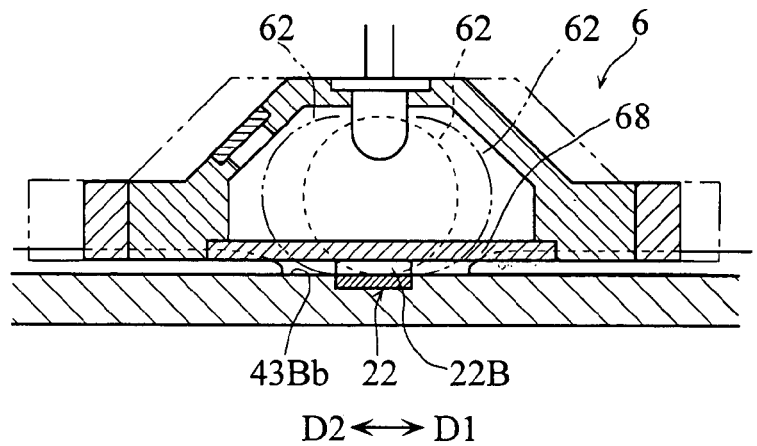

In this process, as shown in FIGS. 13A-13C, until the cleaning pads 22B come to the region of the transparent plate 68 which is directly below the light emitting elements 66, the rollers 62 of the photometry mechanism 6 are located on the rails 43A of the guide portions 43. Therefore, until the cleaning pads 22B come to the above-described region, the entirety of the photometry mechanism 6 is located at a higher position so that the cleaning pads 22B do not come into contact with the photometry mechanism 6. As shown in FIGS. 14A-14C, when the cleaning pads 22B are located at the region of the transparent plate 68 which is directly below the light emitting elements 66, the rollers 62 of the photometry mechanism 6 are located in the second recesses 43Bb of the guide portions 43. Therefore, when the cleaning pads 22B are located at the above-described region, the entirety of the photometry mechanism 6 is located at a lower position so that the cleaning pads 22B are pressed against the transparent plate 68. Since the cleaning pads 22B are flexible, the cleaning pads 22B are elastically deformed and held in close contact with the transparent plate 68 due to the restoring force.

Then, in the analyzer 1, the transparent plate 68 is heated, as shown in FIG. 12 (S63). Specifically, the transparent plate 68 may be heated by a heater used in causing reaction between the sample and the reagent of the reagent pads 20B and 21B of the test pieces 20 and 21. The heating temperature of the transparent plate 68 may be set to the reaction temperature of the sample and the reagent (e.g. 30 to 40° C.). As noted before, the cleaning pads 22 are held in close contact with the transparent plate 68 and impregnated with the cleaning liquid. Thus, when the transparent plate 68 is heated, the cleaning liquid infiltrates into the dirt on the transparent plate 68, causing the dirt to come to the surface.

Then, in the analyzer 1, the dirt is wiped off the transparent plate 68 by the cleaning pads 22B (S64). As shown in FIG. 14C, the wiping of the dirt is performed by moving the test piece table 4 reciprocally in the directions D1, D2 a predetermined number of times. Since the dirt of the transparent plate 68 has come to the surface due to the heating of the transparent plate 68 in S63, the dirt is properly removed by the wiping.

After the wiping of the dirt (S64) is completed, checking of the transparent plate 68 for dirt is performed (S65). The dirt checking (S65) is performed similarly to the above-described step S2 (see FIGS. 10 and 11).

When the transparent plate 68 is determined to be dirty in S66 (S66: YES), the wiping of dirt in S64 and the dirt checking in S65 are repeated until it is determined in S66 that the transparent plate 68 is not dirty (S66: NO) or it is determined that the wiping is performed a predetermined number of times (S67: YES).

Since the dirt checking is performed (S65) after the wiping of the dirt (S64), even when dirt cannot be removed sufficiently by the single wiping, dirt is reliably removed from the transparent plate 68 by the wiping (S64) performed thereafter. Further, when the dirt cannot be removed sufficiently, the analyzer notifies the user that the accurate measurement may not be possible.

When it is determined in S66 that the transparent plate 68 is not dirty (S66: NO) or it is determined that the wiping of the dirt (S64) is performed a predetermined number of times (S67: YES), the analyzer gives a notice to that effect (S68). Specifically, when it is determined in S66 that the transparent plate 68 is not dirty (S66: NO), the analyzer gives a notice in S68 that the dirt is properly removed from the transparent plate 68. When it is determined in S67 that the wiping (S64) is performed a predetermined number of times (S67: YES), the analyzer gives a notice in S68 that the dirt is not sufficiently removed from the transparent plate 68. Such notices can be given by displaying a code or a sentence representing the notice at the display 38.

Then, in the analyzer 1, whether or not the cleaning tool 22 is removed from the first slit 41 of the test piece table 4 is determined (S69). When it is determined that the cleaning tool 22 is not removed (S69: NO), the determination of S69 and S70 is repeated until a predetermined time elapses from the notice in S68 (S70: YES) or until it is determined that the cleaning tool 22 is removed (S69: YES).

When it is determined in S69 that the cleaning tool 22 is removed (S69: YES), the cleaning process is finished. Further, when it is determined in S61 that the cleaning tool 22 is not placed even after the lapse of a predetermined time from the selection of the cleaning mode (S61: YES) or when it is determined that the cleaning tool 22 is not removed after the lapse of a predetermined time from the notice in S68 (S70:

YES), the analyzer gives a notice to that effect (S71) and then finishes the cleaning process. Specifically, when it is determined in S61 that the cleaning tool 22 is not placed even after the lapse of a predetermined time (S61: YES), the analyzer gives a notice in S71 that the cleaning is not performed properly because the cleaning tool 22 is not placed. When it is determined in S61 that the cleaning tool 22 is not removed even after the lapse of a predetermined time (S70: YES), the analyzer gives a notice in S71 that the cleaning tool 22 is not removed.

As shown in FIG. 9, when it is determined in S5 that the cleaning mode is not selected (S5: NO) or the cleaning (S6) is finished, the analyzer 1 determines whether or not the analysis mode is selected by the user (S7). The selection of the analysis mode by the user can be performed by operating the operation buttons 37A.

When it is determined that the analysis mode is not selected (S7: NO), the analyzer 1 determines whether or not the cleaning mode is selected (S5) or whether or not the analysis mode is selected (S7).

When it is determined that the analysis mode is selected (S7: YES), the analyzer 1 performs the analysis (S8).

Figure 15:
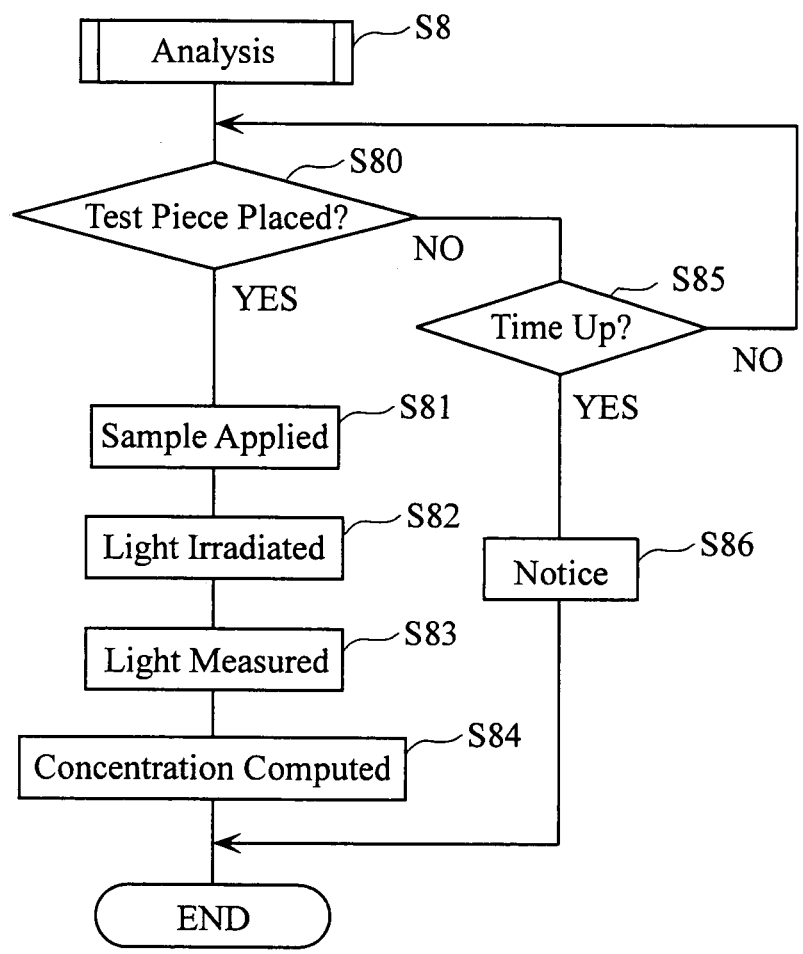
FIG. 15 is a flowchart for describing the analysis process of the analyzer shown in FIG. 1.

As shown in FIG. 15, in the analysis process (S8), the analyzer 1 first determines whether or not the test pieces 20, 21 are placed at the first and the second slits 41, 42 (S80). This determination is performed based on a signal generated by operating the operation buttons 37A by the user. Alternatively, a sensor may be provided at the first and the second slits 41, 42 so that whether or not the test pieces 20, 21 are placed at the first and the second slits 41, 42 can be detected by the sensor.

When it is determined in S80 that the test pieces 20, 21 are placed at the first and the second slits 41, 42 (S80: YES), sample is applied to the reagent pads 20B, 21B of the test pieces 20, 21 (S81). The application of the sample to the reagent pads 20B, 21B is performed by sucking the sample into the tip 52 attached to the nozzle 50 of the dispenser 5 and then discharging the sample onto the reagent pads 20B, 21B (see FIG. 2). The reagent pads 20B and 21B contain a reagent for reaction with a particular component. Therefore, when the sample is applied to the reagent pads 20B and 21B (S81), the reagent reacts with a particular component in the sample at the reagent pads 20B and 21B. As a result, the reagent pads 20B and 21B develop a color corresponding to the amount of the particular component.

Figure 16:
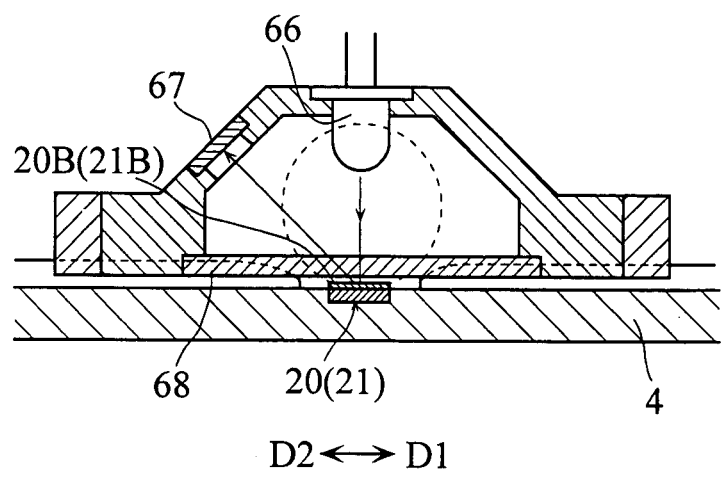
FIG. 16 is a sectional view of a principal portion for describing the operation of the analyzer in the analysis process.
Figure 17:
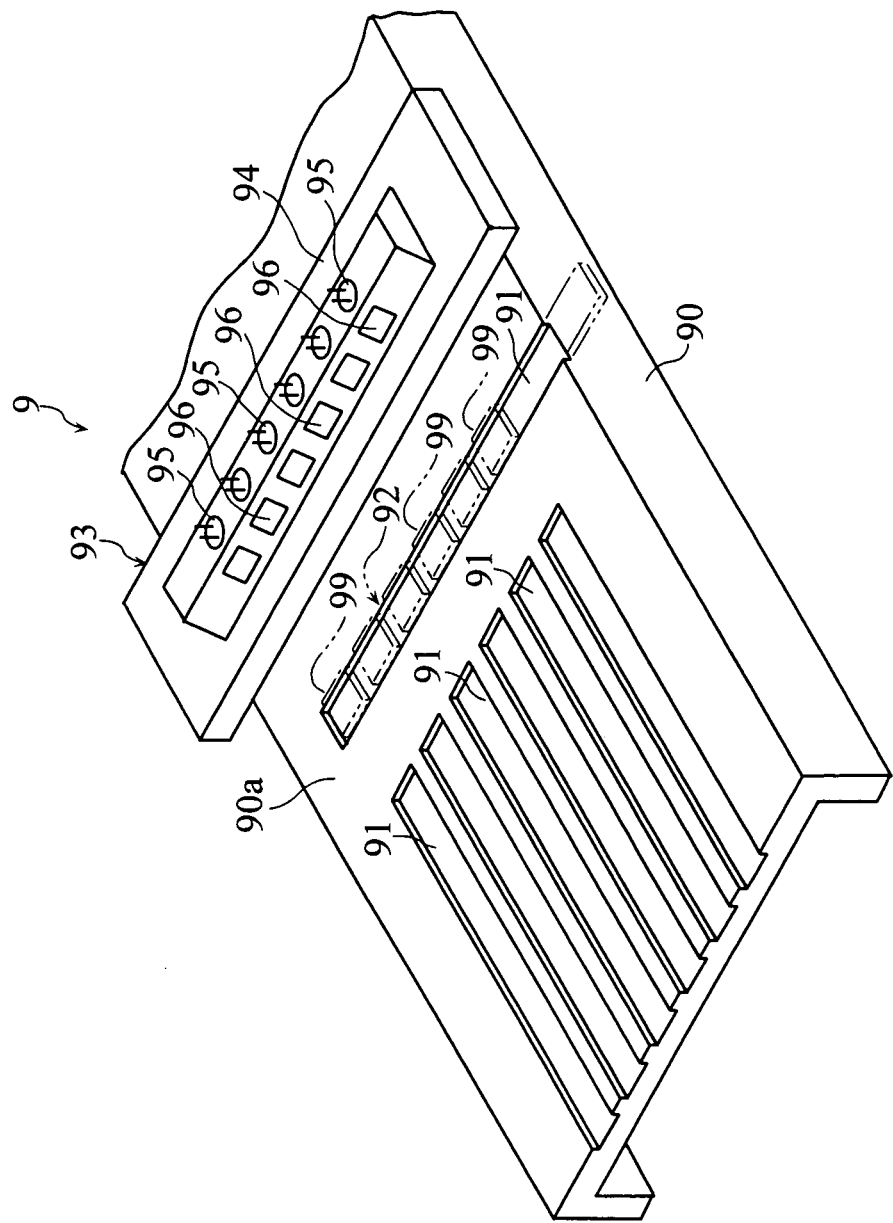
FIG. 17 is a perspective view showing a principal portion of a conventional analyzer.
Figure 18:
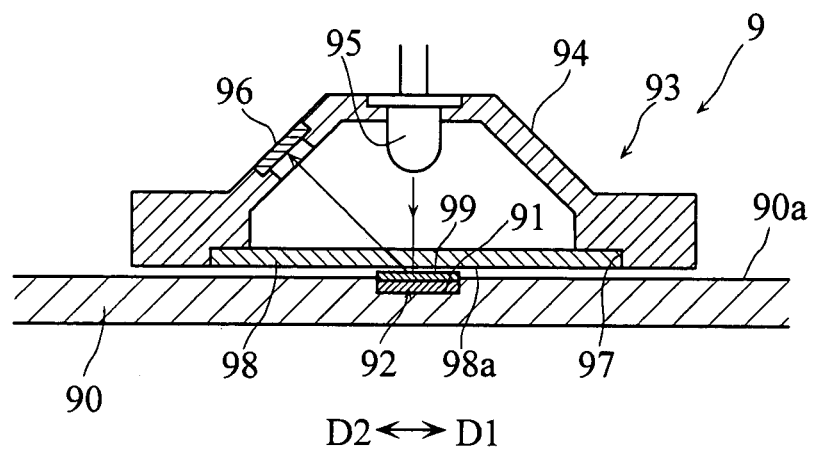
FIG. 18 is a sectional view of a principal portion of the analyzer shown in FIG. 17.

After the application of the sample (S81) is finished, the test piece table 4 is moved in the direction D1 as shown in FIG. 16 so that the reagent pads 20B and 21B of the test pieces 20 and 21 face the transparent plate 68 of the photometry mechanism 6. In this state, the reagent pads 20B and 21B are irradiated with light from the light emitting elements 66 (S82). In the analyzer 1, the amount of light reflected at the reagent pads 20B and 21B and received by the light receiving elements 67 is measured (S83). Based on the measurements, the concentration of the particular component in the sample is computed (S84).

The concentration computed in this way is displayed at the display 38 or printed on non-illustrated recording paper. Further, in the cleaning step (S6), when it is determined that the dirt is not sufficiently removed from the transparent plate 68 (S66: NO) or when the cleaning is finished without wiping off the dirt (S61: YES) or when the analysis mode is selected (S7: YES) without selecting the cleaning mode (S5: NO) although the transparent plate 68 is determined to be dirty (S3: YES) the notice that the analysis result may not be accurate may be added.

In the above-described analyzer 1, the transparent plate 68 of the photometry mechanism 6 is checked for dirt when the power source is turned on, and when the transparent plate 68 is dirty, a notice that the cleaning of the transparent plate 68 is necessary is given. Thus, the analyzer 1 informs the user of the fact that the cleaning is necessary (the fact that accurate analysis may not be possible). Therefore, the possibility that the user performs sample analysis in the state in which the transparent plate 68 is dirty is reduced, so that the accuracy of sample analysis is increased.

Further, the cleaning of the transparent plate 68 is performed automatically in the analyzer 1 just by selecting the cleaning mode by e.g. operating the operation buttons 37A and placing the cleaning tool 22 on the test piece table 4. Therefore, the burden on the user in cleaning the transparent plate 68 is reduced, so that the possibility that the user neglects the cleaning reduces. Further, since the cleaning is performed automatically by the apparatus, the degree of cleaning does not differ from user to user. Therefore, in the analyzer 1, as compared with the case where the user manually cleans the transparent plate 68, the accuracy of analysis improves.

The present invention is not limited to the structure employed in the foregoing embodiment. For instance, the structure for moving the photometry mechanism 6 up and down relative to the test piece table 4 is not limited to the example described as the analyzer 1, and other structures may be employed. It is only necessary that the photometry mechanism 6 is movable up and down relative to the test piece table 4. Therefore, the test piece table 4 may be movable up and down or both of the photometry mechanism 6 and the test piece table 4 may be movable up and down.

Further, use may be made of a cleaning tool in which the portions to which the cleaning liquid is to be applied (wet pads) and the portions to which the cleaning liquid is not to be applied (dry pads) are aligned in the width direction of the substrate. Moreover, the cleaning tool does not necessarily need to have a porous structure having water absorbency. Further, the portion to be pressed against the transparent plate of the photometry mechanism (press portion) does not necessarily need to be in the form of a pad. For instance, the press portion may be in the form of a non-porous pad made of e.g. rubber, may be in the form of a brush made of a plurality of linear strips or may have a shape extending in the longitudinal direction of the substrate.

The invention claimed is:

1. An analyzer in combination with a cleaning tool, the analyzer comprising:
    a photometry mechanism including a light emitting surface or a light incident surface for photometrically analyzing a reagent pad of an analytical tool with a sample applied to the reagent pad; and
    a table including an analyzing position at which the analytical tool is placed for analysis;
    wherein the cleaning tool is configured to be placed at the analyzing position in exchange for the analyzing tool and includes a press portion that is pressed against the light emitting surface or the light incident surface for cleaning when the photometry mechanism is located at a position corresponding to the analyzing position; and
    wherein the analyzing position is provided by a slot formed on the table for exchangeable fitting the analyzing tool or the cleaning tool.

2. The analyzer according to claim 1, wherein the press portion is configured to rub the light emitting surface or the light incident surface.

3. The analyzer according to claim 1, wherein the photometry mechanism is movable up and down relative to the table.

4. The analyzer according to claim 1, wherein the table includes a guide extending in a movement direction of the table and including a recess,
   wherein the photometry mechanism includes a contact portion for corning into contact with the guide,
   wherein the contact portion is received in the recess when the photometry mechanism is located at the analyzing position.

5. The analyzer according to claim 1, wherein the light emitting surface or the light incident surface is heated when the press portion is impregnated with a cleaning liquid and pressed against the light emitting surface or the light incident surface.

6. The analyzer according to claim 1, wherein the cleaning tool comprises a base plate for fitting in the slot of the table and a cleaning pad carried by the base plate for coming into pressing contact with the light emitting surface or the light incident surface.

7. The analyzer according to claim 1, wherein the cleaning tool comprises a base plate for fitting in the slot of the table and a plurality of cleaning pads carried by the base plate for corning into pressing contact with the light emitting surface or the light incident surface.

8. The analyzer according to claim 6, wherein the analytical tool comprises a substrate for fitting in the slot of the table and a reagent pad, the cleaning pad of the cleaning tool having a larger thickness than the reagent pad of the analytical tool.

\* \* \* \* \*